United States Patent [19]
Laske

[11] Patent Number: 5,957,967
[45] Date of Patent: Sep. 28, 1999

[54] IMPLANTABLE MEDICAL LEAD USING STAMPED CONDUCTOR AND DISTAL LOOP

[75] Inventor: Timothy G. Laske, Shoreview, Minn.

[73] Assignee: Medtronic, Inc., Minneapolis, Minn.

[21] Appl. No.: 09/026,536

[22] Filed: Feb. 19, 1998

[51] Int. Cl.⁶ ............................... A61N 1/05; A61N 1/04
[52] U.S. Cl. ........................ 607/125; 607/119; 607/122
[58] Field of Search ........................... 607/119, 122, 607/126, 125

[56] References Cited

U.S. PATENT DOCUMENTS

| | | |
|---|---|---|
| 3,035,583 | 5/1962 | Hirsch et al. . |
| 3,348,548 | 10/1967 | Chardack . |
| 3,416,533 | 12/1968 | Fisher et al. . |
| 3,731,376 | 5/1973 | Ackerman . |
| 4,026,303 | 5/1977 | Babotai . |
| 5,246,014 | 9/1993 | Williams et al. . |
| 5,282,844 | 2/1994 | Stokes et al. . |
| 5,282,845 | 2/1994 | Bush et al. ............................... 607/128 |
| 5,336,254 | 8/1994 | Brennen et al. . |
| 5,584,873 | 12/1996 | Shoberg et al. . |
| 5,755,765 | 5/1998 | Hyde et al. . |
| 5,836,947 | 11/1998 | Fleischman et al. . |
| 5,897,554 | 4/1999 | Chia et al. . |

FOREIGN PATENT DOCUMENTS 1219017   1/1971   United Kingdom .

Primary Examiner—William E. Kamm
Assistant Examiner—Carl H. Layno
Attorney, Agent, or Firm—Reed A. Duthler; Harold R. Patton

[57] ABSTRACT

An implantable electrical lead having an elongated insulative lead body with a longitudinal lumen therein extending from the proximal end of the lead body to a distal portion of the lead body and having an elongated stranded electrical conductor located in the lumen, the conductor having a distal end which exits the lumen at the distal portion of the lead body and which is curved to form a loop exterior to the distal portion of the lead body and which then re-enters the lead body. In some embodiments, the strands of the conductor are twisted helically in a first direction and the conductor is twisted in a second, opposite direction in that portion of the conductor located exterior to the lead body to separate strands of the conductor. The stranded conductor may exit the lumen at the distal end of the lead body or at one or more locations proximal to the distal end of the lead body.

15 Claims, 3 Drawing Sheets

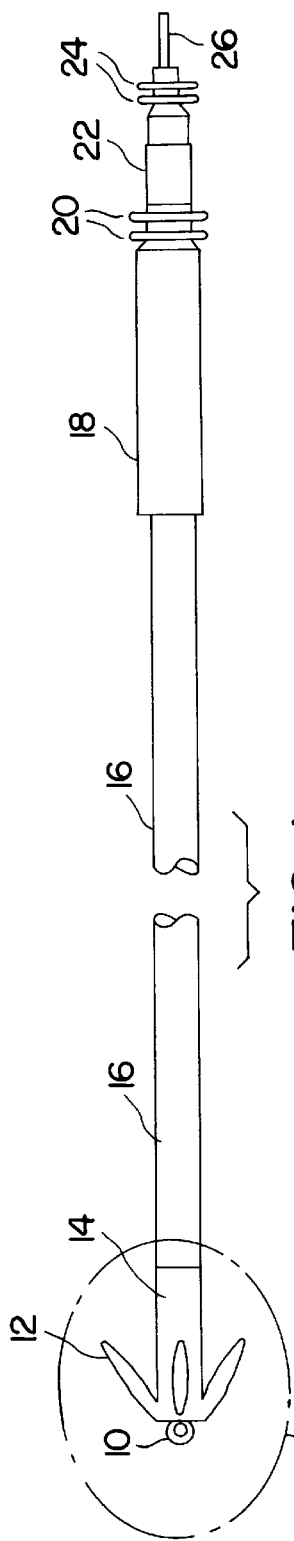
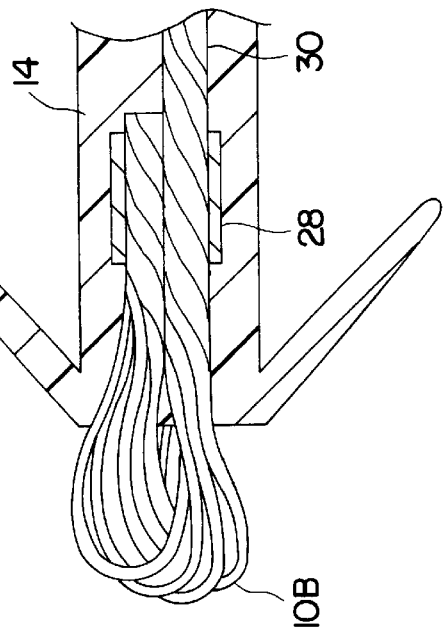
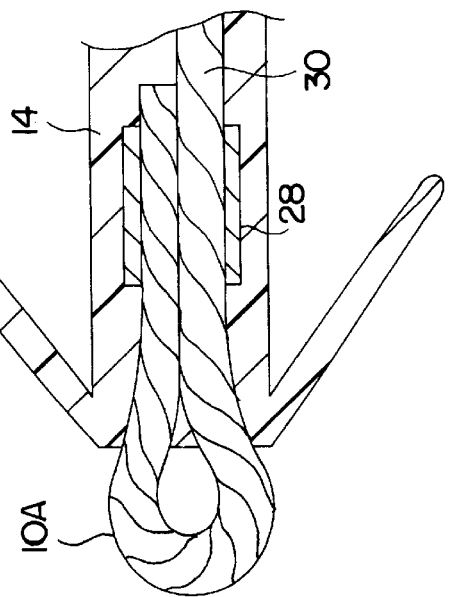
FIG. 1
FIG. 2
FIG. 3

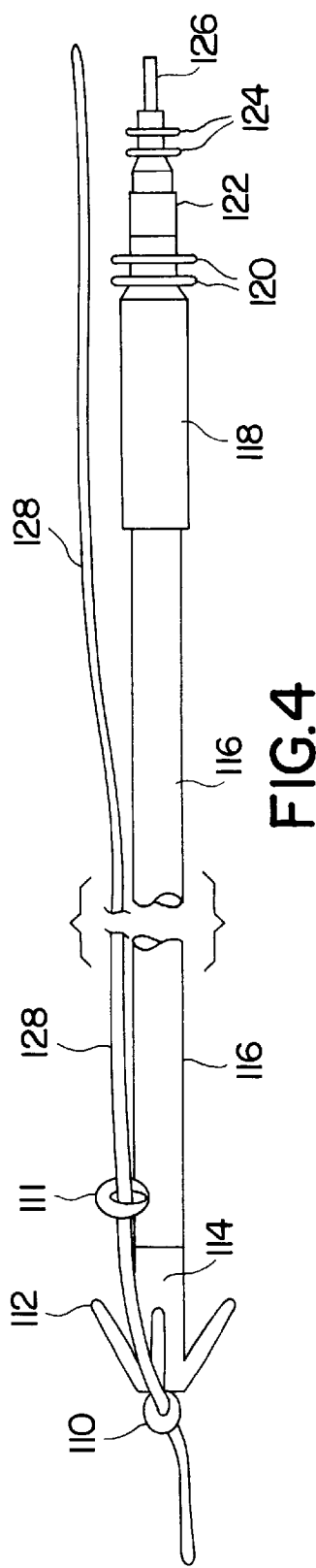
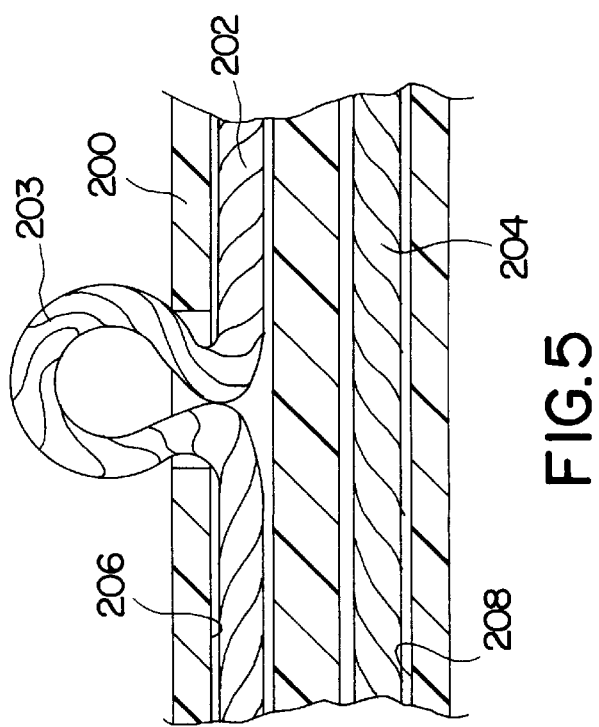

IMPLANTABLE MEDICAL LEAD USING STAMPED CONDUCTOR AND DISTAL LOOP

BACKGROUND OF THE INVENTION

The present invention relates to medical leads generally and more particularly to implantable cardiac pacing leads.

In the context of permanently implantable cardiac pacing leads, the pacing electrodes mounted to the leads have typically taken the form of a solid metal electrode body coupled to a separately formed coiled metal conductor. For example, as disclosed in U.S. Pat. No. 3,348,548 issued to Chardack and U.S. Pat. No. 5,282,844 issued to Stokes. More recently, there has been a renewed interest in cabled or stranded conductors in the context of cardiac pacing leads, for example as disclosed in U.S. Pat. No. 5,584,873 issued to Shoberg et al. and U.S. Pat. No. 5,246,014 issued to Williams et al.

In the early days of pacing, it was proposed that pacing electrodes could take the form of a continuation of the conductor within the pacing lead body. For example, U.S. Pat. No. 3,804,098 issued to Friedman employs an extension of a tinsel wire conductor as a pacing electrode. Alternatively, a stranded wire, exposed to the distal end of the lead and filled with silver has been proposed as a pacing electrode in U.S. Pat. No. 3,731,376 issued to Ackerman. Simply extending an uninsulated portion of a coiled or stranded conductor to serve as an electrode is disclosed in U.S. Pat. No. 3,416,533 issued to Fisher et al and U.S. Pat. No. 3,035,583 issued to Hirsch et al., respectively. Extending a braided carbon fiber conductor to serve as a pacing or defibrillation electrode is disclosed in British Patent No. 1,219,017 issued to Thompson-Telco and U.S. Pat. No. 5.336,254 issued to Brennen et al., respectively.

SUMMARY OF THE INVENTION

The present invention is directed to an improved pacing lead in which the pacing electrode is formed integral to the conductor within the lead body. In particular, the present invention may employ a cabled conductor as described in U.S. Pat. No. 5,584,873 issued to Shoberg et al, incorporated herein by reference in its entirety, having seven strands, six strands wound around the seventh strand, each strand formed of seven wires. A portion of the cabled conductor is extended out of the lead body to form a loop, and re-enters the lead body in order to maintain the configuration of the loop. The cable typically extends distally within a lumen in the lead body from a connector assembly located on the proximal end of the lead body to an exit point and re-enters the lead body either at the exit point or at a different point. The cable may continue distally from its point of re-entry or may be coupled to the proximally extending portion of the cable. The cable may exit and re-enter the lead body only once or may do so a number of times.

The exposed, looped portion of the cabled conductor provides a high surface area for purposes of sensing cardiac depolarizations, while retaining a small overall geometric area to provide a relatively high pacing impedance. If the cable exits through a side of the lead body, the laterally extending looped configuration may also be beneficial in providing improved electrode contact in leads intended for use in the coronary sinus/great vein or other blood vessels. In addition, the structure of the looped cable allows for tissue ingrowth to permanently stabilize electrode in a desired location relative to heart tissue. The looped cable electrode may be employed with or without other fixation mechanisms such as tines and may be employed as either the pacing cathode or pacing anode or both. If desired, the exposed looped portion of the cable may be platinized or otherwise treated to increase the effective surface area of the electrode for sensing purposes. The looped portions of the cable may also be employed in conjunction with an external guidewire or stylet to assist in lead placement.

BRIEF DESCRIPTION OF THE DRAWINGS

FIG. 1 is a plan view of the lead according to the present invention.

FIG. 2 is a sectional view through the distal end of the lead incorporating the present invention, illustrating a first embodiment of the looped cable electrode.

FIG. 3 is a cross-sectional view through a second embodiment of a lead according to the present invention illustrating a second embodiment of the looped cable electrode.

FIG. 4 is a plan view of a lead according to the present invention employing looped cable electrodes as both the pacing anode and pacing cathode.

FIG. 5 is a cross section through a third embodiment of according to the present invention illustrating a third embodiment of the looped cable electrode.

DETAILED DESCRIPTION OF THE PREFERRED EMBODIMENT

Figure 6:
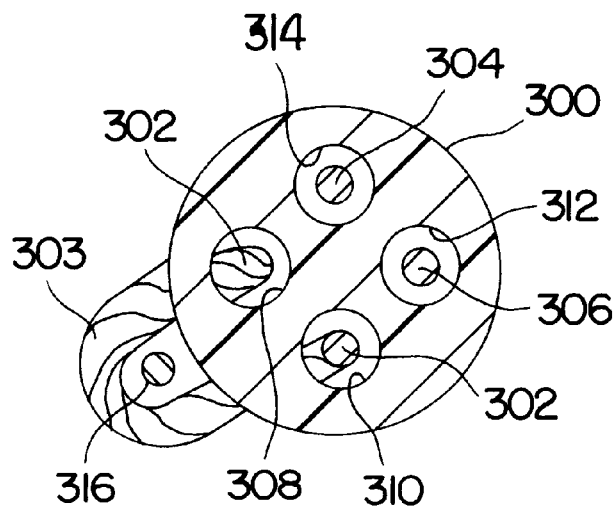
FIG. 6 is a cross section through a fourth embodiment of according to the present invention illustrating a fourth embodiment of the looped cable electrode.

FIG. 1 is a plan view of a lead according to the present invention. The looped cabled electrode 10 is shown extending from the distal end of the lead body, emerging from tine sheath 14 which also carries pliant tines 12 useful for acute fixation of the lead in a desired position within the heart. Tine sleeve 14 is molded of an insulative biocompatible plastic such as silicone rubber or polyurethane and is affixed to the distal end of insulative lead body 16. The cabled conductor of which looped electrode 10 is formed extends proximally within insulative lead body 16 to connector assembly 18. Connector assembly 18 is an IS-1 type connector, and carries sealing rings 20, connector ring 22, sealing rings 24 and connector pin 26. Connector pin 26 is coupled to the cabled conductor of which electrode 10 is fabricated. In the embodiment illustrated, connector ring 22 is not electrically coupled to any other component of the lead. However, in alternate embodiments, connector ring 22 may be coupled to an additional pacing electrode, a defibrillation or cardioversion electrode, or a sensor. Because the cabled conductor of which electrode 10 is a part extends continuously from connector pin 26 to the distal end of the lead, the lead is essentially inextensible, and also capable of withstanding high tractional forces. As such, should the lead be required to be removed, it is by virtue of its design inherently reinforced along its length, assisting in preventing separation or partial disassembly of the lead during extraction procedures.

FIG. 2 is a cross-sectional view through the distal portion of the lead of FIG. 1, illustrating a first embodiment of a looped electrode 10A, according to the present invention. An elongated stranded conductor 30 extends from the proximal end of the lead and exits the distal portion of tine sleeve 14, where it is looped back upon itself and coupled to itself by means of a crimp sleeve 28. Crimp sleeve 28 may be configured so that the distal end of cabled conductor 30 is permanently electrically and mechanically coupled to the adjacent portion of the conductor. An additional alternative embodiment, crimp sleeve 28 may be dispensed within its entirety, and the engagement of cabled conductor 30 with tine sleeve 14, in and of itself, is relied upon to maintain the distal end of cabled conductor 30 within tine sleeve 14. In this alternative embodiment, it is possible to pull the distal end of cabled conductor 30 out of crimp sleeve 28 and out of tine sleeve 14 so that if tissue has grown through the loop, the lead is more readily extracted. Whether tine sleeve 14 is molded of silicone rubber or polyurethane, it may either be molded around the assembly of conductor 30 and crimp sleeve 28 or may be separately molded and later applied to the assembly of conductor 30 and crimp sleeve 28. If desired, the exposed looped electrode portion 10A of the cable may be platinized or otherwise treated to increase the effective surface area of the electrode for sensing purposes.

FIG. 3 shows an alternative embodiment of a lead according to the present invention illustrating a second embodiment of a looped electrode 10B. In this embodiment, the conductor 30 is twisted opposite to the direction of winding of the individual strands or bundles of wires within the cable in order to separate the individual strands or bundles, prior to crimping of the distal end of the cable to itself by means of crimp sleeve 28. In this embodiment, the electrode displays an even more increased surface area for purposes of sensing of electrical signals, while retaining an overall relatively small microscopic area for purposes of maintaining relatively high pacing impedances.

FIG. 4 is a plan view of an alternative embodiment of a lead according to the present invention. A first looped cable electrode 110 is shown extending from the distal end of the lead body, emerging from tine sheath 114 which also carries pliant tines 112. The cabled conductor of which looped electrode 110 is formed extends proximally within insulative lead body 116 to connector assembly 118. A second looped cable electrode 111 is shown extending laterally from the distal portion of the lead body, emerging proximal to tine sheath 114. The cabled conductor of which looped electrode 111 is formed extends also proximally within insulative lead body 116 to connector assembly 118 and is insulated from the cabled conductor forming electrode 110. Connector assembly 118 is an IS-1 type connector, and carries sealing rings 120, connector ring 122, sealing rings 124 and connector pin 126. Connector pin 126 is coupled to the cabled conductor of which electrode 110 is fabricated. Connector ring 122 is coupled to the cabled conductor of which electrode 111 is fabricated. As illustrated, looped cable electrodes 110 and 111 serve to allow the lead to be advanced over a guidewire 128, which passes sequentially through the loops of both electrodes. Typically, a guide catheter would be employed in conduction with guidewire 128 to advance the lead to its desired location within the heart.

FIG. 5 illustrates a cross section through a portion of the lead according to a third embodiment of the present invention. In this embodiment, the lead body 200 is a multi-lumen lead body, for example provided with four orthogonally located lumens, two of which, lumens 206 and 208 are visible in this view. The first cable conductor 202 exits lead body 200 to form a loop 203, reenters the lead body and continues distally from loop 203 within lumen 206. A second stranded conductor 204 is illustrated in lumen 208. The distal end of electrode 202 may terminate a short distance distally of loop 203, or may continue from loop 203 to the distal end of the lead, where it may be coupled to or employed as an additional electrode.

FIG. 6 is a cross-sectional view of a fourth embodiment of a lead according to a present invention. In this view it can be seen that the lead body 400 is provided with four orthogonally located lumens 308, 310, 312 and 314. Lumens 312 and 314 each carry a stranded conductor, 304 and 306, respectively. Stranded conductor 302 extends from the proximal end of the lead within lumen 308, exits the lead body 300 to form a loop 303. Rather than reentering lumen 308, conductor 302 reenters the lead body and extends distally from loop 303 within lumen 310, providing a loop which lies in a plane relatively perpendicular to the axis of lead body 300. This configuration is particularly desirable if the loop is to be used as a guide for an external stylet or guidewire 316 (illustrated in cross-section). Conductor 302 may extend for only a short period distal to loop 303, or may extend to the distal end of the lead where it may be served as or coupled to an additional electrode.

Figure 7:
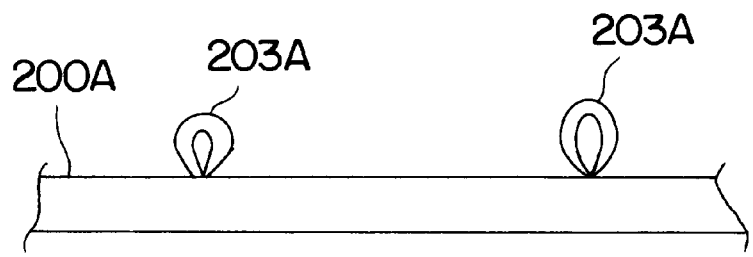
FIG. 7 is a plan view of a potion of lead body employing multiple looped cable electrodes according to the embodiment illustrated in FIG. 5.
Figure 8:
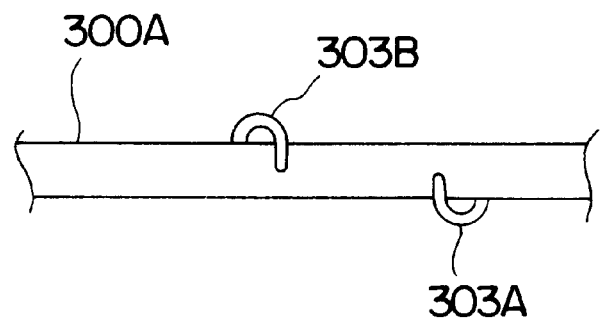
FIG. 8 is a plan view of a potion of lead body employing multiple looped cable electrodes according to the embodiment illustrated in FIG. 8.

FIGS. 7 and 8 illustrate embodiments of leads in which a cabled conductor exits and reenters the lead body at multiple locations at multiple locations along the lead. FIG. 7 illustrates a lead having looped cable electrodes formed in the fashion illustrated in FIG. 5. Lead body 200A is provided with first and second loops 203A and may be provided with additional loops. These multiple loops may be used as electrodes and/or as guide loops for an associated external stylet or guidewire.

FIG. 8 illustrates a lead having multiple loops formed according to FIG. 6 in the embodiment illustrated, the cabled conductor exits a first lumen within a lead body to form loop 303A, and reenters the lead body and extends distally from loop 303A within a second lumen within the lead body. The conductor again exits the lead body to form a second loop 303B, thereafter reenters the lead body and extends distally from loop 303B within a third lumen within the lead body. Alternatively, the conductor might reenter the lead body and extend distally from loop 303B within the first lumen, providing a second loop generally perpendicular to the axis of the lead body, aligned with loop 303A. This configuration is believed particularly beneficial for use in conjunction with an external stylet or guidewire.

In addition to entering and exiting the lead body a number of times to form multiple electrodes, the conductor also may exit and reenter the lead body at multiple, closely spaced locations, in order to effectively provide an elongated electrode surface. If all loops are located aligned with one another along one side of the lead body, exiting and entering the lead body at closely spaced locations, the lead is effectively provided with a directional, elongated electrode which might be particularly advantageous in the context of defibrillation leads for use in the coronary sinus, allowing direction of the field produced by the electrode primarily into heart tissue. Alternatively, the cable may exit and enter the lead body at multiple closely spaced locations, each time entering a different lumen to provide a series of loops arrayed around the circumference of the lead body. In this case, a more omnidirectional elongated electrode surface may be provided.

While the above embodiments of leads according to the present invention take the form of endocardial leads, the present invention is also believed applicable in the context of myocardial or epicardial electrodes. As such, the above disclosed embodiments should be considered exemplary, rather than limiting, with regards to the claims that follow.

In conjunction with the above disclosure, we claim:

1. An implantable electrical lead, comprising:

an elongated insulative lead body having a longitudinal first lumen therein extending from a proximal end of the lead body to a distal portion of the lead body;

an electrical connector mounted to the proximal end of the lead body; and a single, continuous elongated stranded electrical conductor located in the first lumen, having a proximal end coupled to the electrical connector and a distal end which exits the lumen at the distal portion of the lead body, which distal end is curved to form a loop exterior to the distal portion of the lead body and which re-enters the lead body.

2. An implantable electrical lead, comprising:

an elongated insulative lead body having a longitudinal first lumen therein extending from a proximal end of the lead body to a distal portion of the lead body;

an electrical connector mounted to the proximal end of the lead body; and an elongated stranded electrical conductor located in the first lumen having a proximal end coupled to the electrical connector and a distal end which exits the lumen at the distal portion of the lead body, which distal end is curved to form a loop exterior to the distal portion of the lead body and which re-enters the lead body; and wherein strands of the conductor are twisted helically in a first direction and wherein the conductor is twisted in a second, opposite direction in that portion of the conductor located exterior to the lead body to separate strands of the conductor.

3. A lead according to claim 1 or claim 2 wherein said distal end of the conductor is mechanically and electrically coupled to a more proximal portion of the conductor, within the first lumen.

4. A lead according to claim 1 or claim 2 wherein a portion of the distal end of the conductor which re-enters the lead body extends distally from the loop, within said first lumen.

5. A lead according to claim 1 or claim 2 wherein a portion of the distal end of the conductor which re-enters the lead body extends proximally from the loop, within said first lumen.

6. A lead according to claim 1 or claim 2 wherein the lead body further has a longitudinal second lumen and wherein said distal end of the conductor extends from the loop within said second lumen.

7. A lead according to claim 1 or claim 2 wherein the conductor comprises a cabled conductor.

8. A lead according to claim 1 or claim 2 wherein the conductor exits the lumen at a portion of the lead body, proximal to a distal end of the lead body.

9. A lead according to claim 1 or claim 2 wherein the conductor exits and reenters enters the lead body at multiple locations.

10. An implantable electrical lead system, comprising:

an elongated insulative lead body having a longitudinal first lumen therein extending from a proximal end of the lead body to a distal portion of the lead body adjacent a distal end of the lead body;

an electrical connector mounted to the proximal end of the lead body;

an elongated electrical conductor located in the first lumen, having a proximal end coupled to the electrical connector and a distal end which exits the lumen at the distal portion of the lead body, which distal end is curved to form a loop exterior to the distal portion of the lead body and which reenters the lead body; and a guidewire, extending through the loop formed by the conductor.

11. A system according to claim 10 wherein said conductor comprises a stranded conductor.

12. A lead according to claim 10 or claim 11 wherein the conductor exits the lumen at a distal portion of the lead body, proximal to a distal end of the lead body.

13. A lead according to claim 10 or claim 11 wherein the distal end of the conductor extends from the loop in the first lumen.

14. A lead according to claim 10 or claim 11 wherein the lead body further has a second lumen and wherein the distal end of the conductor extends from the loop in the second lumen.

15. A lead according to claim 10 or claim 11 wherein the conductor exits and re-enters the lead body at multiple locations.

* * * * *